US009604936B2

(12) United States Patent
Witowski et al.

(10) Patent No.: US 9,604,936 B2
(45) Date of Patent: *Mar. 28, 2017

(54) BESYLATE SALT OF A BTK INHIBITOR

(71) Applicant: Celgene Avilomics Research, Inc., Bedford, MA (US)

(72) Inventors: Steven Richard Witowski, Madison, NJ (US); William Frederick Westlin, III, Boxborough, MA (US); Richland Wayne Tester, Marlborough, MA (US)

(73) Assignee: Celgene CAR LLC, Pembroke (BM)

( * ) Notice: Subject to any disclaimer, the term of this patent is extended or adjusted under 35 U.S.C. 154(b) by 36 days.

This patent is subject to a terminal disclaimer.

(21) Appl. No.: 14/058,847

(22) Filed: Oct. 21, 2013

(65) Prior Publication Data

US 2014/0057929 A1    Feb. 27, 2014

Related U.S. Application Data

(63) Continuation of application No. 13/205,062, filed on Aug. 8, 2011, now Pat. No. 8,563,568.

(60) Provisional application No. 61/372,349, filed on Aug. 10, 2010.

(51) Int. Cl.
*C07D 239/48* (2006.01)
*A61K 31/506* (2006.01)

(52) U.S. Cl.
CPC .......... *C07D 239/48* (2013.01); *A61K 31/506* (2013.01)

(58) Field of Classification Search
CPC ................ C07D 239/48; A61K 31/506
USPC .......................................... 544/323; 514/275
See application file for complete search history.

(56) References Cited

U.S. PATENT DOCUMENTS

| 4,032,637 | A | * | 6/1977 | Spiegel et al. ............. 514/225.5 |
|---|---|---|---|---|
| 4,879,303 | A | * | 11/1989 | Davison et al. ............. 514/356 |
| 5,453,510 | A | * | 9/1995 | Hill et al. .................. 546/140 |
| 5,958,935 | A | | 9/1999 | Davis et al. |
| 6,093,716 | A | | 7/2000 | Davis et al. |
| 6,114,333 | A | | 9/2000 | Davis et al. |
| 6,127,376 | A | | 10/2000 | Davey et al. |
| 6,160,010 | A | | 12/2000 | Uckun et al. |
| 6,262,088 | B1 | | 7/2001 | Phillips |
| 6,432,963 | B1 | | 8/2002 | Hisamichi et al. |
| 6,469,168 | B1 | * | 10/2002 | Ratzne Simonek et al. . 544/296 |
| 6,579,983 | B1 | | 6/2003 | Batchelor et al. |
| 6,593,326 | B1 | | 7/2003 | Bradbury et al. |
| 6,838,464 | B2 | | 1/2005 | Pease et al. |
| 6,939,874 | B2 | | 9/2005 | Harmange et al. |
| 7,060,827 | B2 | | 6/2006 | Singh et al. |
| 7,122,542 | B2 | | 10/2006 | Singh et al. |
| 7,125,879 | B2 | | 10/2006 | Guillemont et al. |
| 7,176,212 | B2 | | 2/2007 | Breault et al. |
| 7,202,033 | B2 | | 4/2007 | Prescott et al. |
| 7,241,769 | B2 | | 7/2007 | Stadtmueller et al. |
| 7,282,504 | B2 | | 10/2007 | Armistead et al. |
| 7,329,671 | B2 | | 2/2008 | Singh et al. |
| 7,329,672 | B2 | | 2/2008 | Singh et al. |
| 7,332,484 | B2 | | 2/2008 | Singh et al. |
| 7,435,814 | B2 | | 10/2008 | Singh et al. |
| 7,452,879 | B2 | | 11/2008 | Singh et al. |
| 7,485,724 | B2 | | 2/2009 | Singh et al. |
| 7,491,732 | B2 | | 2/2009 | Li et al. |
| 7,498,435 | B2 | | 3/2009 | Singh et al. |
| 7,504,396 | B2 | | 3/2009 | Nunes et al. |
| 7,514,444 | B2 | | 4/2009 | Honigberg et al. |
| 7,514,445 | B2 | | 4/2009 | Freyne et al. |
| 7,514,446 | B2 | | 4/2009 | Davis-Ward et al. |
| 7,517,886 | B2 | | 4/2009 | Singh et al. |
| 7,528,143 | B2 | | 5/2009 | Noronha et al. |
| 7,531,548 | B2 | | 5/2009 | Guillemont et al. |
| 7,550,460 | B2 | | 6/2009 | Singh et al. |
| 7,557,210 | B2 | | 7/2009 | Singh et al. |
| 7,582,648 | B2 | | 9/2009 | Singh et al. |
| 7,589,200 | B2 | | 9/2009 | Singh et al. |
| 7,642,351 | B2 | | 1/2010 | Singh et al. |
| 7,655,797 | B2 | | 2/2010 | Singh et al. |
| 7,718,662 | B1 | | 5/2010 | Chen et al. |
| 7,741,330 | B1 | | 6/2010 | Chen et al. |
| 7,803,939 | B2 | | 9/2010 | Singh et al. |
| 7,812,029 | B1 | | 10/2010 | Singh et al. |
| 7,820,819 | B2 | | 10/2010 | Singh et al. |
| 7,825,116 | B2 | | 11/2010 | Singh et al. |
| 7,858,633 | B2 | | 12/2010 | Li et al. |
| 7,884,111 | B2 | | 2/2011 | Argade et al. |
| 7,906,644 | B2 | | 3/2011 | Singh et al. |
| 8,088,781 | B2 | | 1/2012 | Honigberg et al. |
| 8,148,525 | B2 | | 4/2012 | Singh et al. |
| 8,158,621 | B2 | | 4/2012 | Singh et al. |
| 8,188,276 | B2 | | 5/2012 | Singh et al. |
| 8,334,296 | B2 | | 12/2012 | Singh et al. |
| 8,338,439 | B2 | | 12/2012 | Singh et al. |
| 8,450,335 | B2 | | 5/2013 | Singh et al. |
| 8,501,751 | B2 | | 8/2013 | Honigberg et al. |
| 8,557,806 | B2 | | 10/2013 | Singh et al. |

(Continued)

FOREIGN PATENT DOCUMENTS

| AU | 2009251863 A1 | 12/2009 |
|---|---|---|
| CN | 102558149 A | 7/2012 |

(Continued)

OTHER PUBLICATIONS

Stahl et al., eds., Handbook of pharmaceutical salts. Properties, selection and use (Wiley-VCH, 2008), pp. 265-327.*
Serajuddin, Advanced Drug Delivery Reviews 59 (2007) 603-616.*
Liu, Rong, ed., Water-Insoluble Drug Formulation (CRC Press, 2008) Chapter 15 pp. 417-435.*
Bastin et al., Organic Process Research & Development 2000, 4, 427-435.*
Morris, et al., International Journal of Pharmaceutics 105 (1994) 209-217.*

(Continued)

*Primary Examiner* — Deepak Rao
(74) *Attorney, Agent, or Firm* — Choate, Hall and Stewart LLP; Kristen S. Buteau

(57) ABSTRACT

The present invention provides a salt form, and compositions thereof, useful as an inhibitor of one or more protein kinases and which exhibits desirable characteristics for the same.

14 Claims, 10 Drawing Sheets

(56) References Cited

U.S. PATENT DOCUMENTS

| | | | |
|---|---|---|---|
| 8,563,568 B2 * | 10/2013 | Witowski et al. ............ 514/275 |
| 8,609,679 B2 | 12/2013 | Singh et al. |
| 8,710,222 B2 | 4/2014 | Singh et al. |
| 8,735,404 B2 | 5/2014 | Honigberg et al. |
| 8,748,438 B2 | 6/2014 | Honigberg et al. |
| 8,748,597 B2 | 6/2014 | Singh et al. |
| 8,796,255 B2 | 8/2014 | Lee et al. |
| 8,822,685 B2 | 9/2014 | Singh et al. |
| 8,835,430 B2 | 9/2014 | Singh et al. |
| 8,853,397 B2 | 10/2014 | Singh et al. |
| 8,883,435 B2 | 11/2014 | Honigberg et al. |
| 8,883,803 B2 | 11/2014 | Honigberg et al. |
| 8,975,249 B2 | 3/2015 | Lee et al. |
| 9,212,181 B2 | 12/2015 | Singh et al. |
| 9,238,629 B2 | 1/2016 | Lee et al. |
| 9,296,737 B2 | 3/2016 | Singh et al. |
| 9,375,431 B2 | 6/2016 | Lee et al. |
| 2004/0019067 A1 | 1/2004 | Armistead et al. |
| 2004/0023957 A1 | 2/2004 | Wang et al. |
| 2004/0077661 A1 | 4/2004 | Arbiser |
| 2005/0004125 A1 | 1/2005 | Freyne et al. |
| 2005/0014753 A1 | 1/2005 | Ding et al. |
| 2005/0085637 A1 | 4/2005 | Cheung et al. |
| 2005/0209221 A1 | 9/2005 | Nunes et al. |
| 2005/0272083 A1 | 12/2005 | Seshagiri |
| 2006/0030018 A1 | 2/2006 | Zuccola et al. |
| 2006/0079543 A1 | 4/2006 | Sum et al. |
| 2006/0084644 A1 | 4/2006 | Pal et al. |
| 2006/0084645 A1 | 4/2006 | Pal et al. |
| 2006/0100227 A1 | 5/2006 | Baenteli et al. |
| 2006/0148800 A1 | 7/2006 | Stadtmueller et al. |
| 2006/0160803 A1 | 7/2006 | Adams et al. |
| 2006/0247241 A1 | 11/2006 | Garcia-Echeverria et al. |
| 2006/0247262 A1 | 11/2006 | Baenteli et al. |
| 2006/0270694 A1 | 11/2006 | Wong |
| 2006/0293311 A1 | 12/2006 | Li et al. |
| 2007/0010668 A1 | 1/2007 | Davis-Ward et al. |
| 2007/0032493 A1 | 2/2007 | Foley et al. |
| 2007/0066658 A1 | 3/2007 | Chappell |
| 2007/0203161 A1 | 8/2007 | Argade et al. |
| 2007/0203162 A1 | 8/2007 | Li et al. |
| 2007/0259904 A1 | 11/2007 | Noronha et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0167330 A1 | 7/2008 | Luecking et al. |
| 2008/0176866 A1 | 7/2008 | Jautelat et al. |
| 2008/0182852 A1 | 7/2008 | Johnson et al. |
| 2008/0194603 A1 | 8/2008 | Li et al. |
| 2008/0194605 A1 | 8/2008 | Heinrich et al. |
| 2008/0207613 A1 | 8/2008 | Styles et al. |
| 2008/0214501 A1 | 9/2008 | Pan et al. |
| 2008/0260754 A1 | 10/2008 | Li et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0029610 A1 | 2/2010 | Singh et al. |
| 2010/0041677 A1 | 2/2010 | Honigberg et al. |
| 2010/0081679 A1 | 4/2010 | Greul et al. |
| 2010/0088912 A1 | 4/2010 | Higgs et al. |
| 2010/0173285 A1 | 7/2010 | Varmus et al. |
| 2010/0197918 A1 | 8/2010 | Singh et al. |
| 2010/0249092 A1 | 9/2010 | Singh et al. |
| 2010/0254905 A1 | 10/2010 | Honigberg et al. |
| 2011/0039868 A1 | 2/2011 | Honigberg et al. |
| 2011/0105472 A1 | 5/2011 | Greul et al. |
| 2011/0144330 A1 | 6/2011 | Singh et al. |
| 2011/0207736 A1 | 8/2011 | Gray et al. |
| 2011/0224235 A1 | 9/2011 | Honigberg et al. |
| 2011/0245156 A1 | 10/2011 | Sielecki-Dzurdz |
| 2011/0245284 A1 | 10/2011 | Greul et al. |
| 2011/0281322 A1 | 11/2011 | Honigberg et al. |
| 2011/0281850 A1 | 11/2011 | Flynn et al. |
| 2012/0040968 A1 | 2/2012 | Shimada et al. |
| 2012/0065201 A1 | 3/2012 | Honigberg et al. |
| 2012/0071497 A1 | 3/2012 | Buggy et al. |
| 2012/0077832 A1 | 3/2012 | Witowski et al. |
| 2012/0083006 A1 | 4/2012 | Ramsden et al. |
| 2012/0087915 A1 | 4/2012 | Buggy et al. |
| 2012/0088912 A1 | 4/2012 | Honigberg et al. |
| 2012/0094999 A1 | 4/2012 | Gray et al. |
| 2012/0101113 A1 | 4/2012 | Honigberg et al. |
| 2012/0101114 A1 | 4/2012 | Honigberg et al. |
| 2012/0149687 A1 | 6/2012 | Lee et al. |
| 2012/0149722 A1 | 6/2012 | Lee et al. |
| 2012/0157426 A1 | 6/2012 | Lee et al. |
| 2012/0165328 A1 | 6/2012 | Honigberg et al. |
| 2012/0165332 A1 | 6/2012 | Major et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0270237 A9 | 10/2012 | Ramsden et al. |
| 2012/0296089 A1 | 11/2012 | Honigberg et al. |
| 2012/0316135 A1 | 12/2012 | Dalgarno et al. |
| 2012/0329130 A1 | 12/2012 | Honigberg et al. |
| 2013/0035334 A1 | 2/2013 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0137708 A1 | 5/2013 | Garske et al. |
| 2013/0165462 A1 | 6/2013 | Singh et al. |
| 2014/0057929 A1 | 2/2014 | Witowski et al. |
| 2014/0134265 A1 | 5/2014 | Buggy et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0187564 A1 | 7/2014 | Honigberg et al. |
| 2014/0187565 A1 | 7/2014 | Honigberg et al. |
| 2014/0213574 A1 | 7/2014 | Singh et al. |
| 2014/0303154 A1 | 10/2014 | Singh et al. |
| 2014/0303191 A1 | 10/2014 | Buggy et al. |
| 2014/0330007 A1 | 11/2014 | Singh et al. |
| 2014/0371241 A1 | 12/2014 | Buggy et al. |
| 2015/0005297 A1 | 1/2015 | Singh et al. |
| 2015/0025055 A1 | 1/2015 | Lee et al. |
| 2015/0038518 A1 | 2/2015 | Balasubramanian |
| 2015/0126504 A1 | 5/2015 | Singh et al. |
| 2015/0158823 A1 | 6/2015 | Singh et al. |
| 2015/0246040 A1 | 9/2015 | Lee et al. |
| 2016/0130236 A1 | 5/2016 | Lee et al. |

FOREIGN PATENT DOCUMENTS

| | | |
|---|---|---|
| CN | 103159742 A | 6/2013 |
| EP | 1 054 004 A1 | 11/2000 |
| JP | H0741461 A | 2/1995 |
| WO | WO-96/28427 A1 | 9/1996 |
| WO | WO-97/19065 A1 | 5/1997 |
| WO | WO-99/31073 A1 | 6/1999 |
| WO | WO-00/27825 A1 | 5/2000 |
| WO | WO-00/46203 A2 | 8/2000 |
| WO | WO-00/78731 A1 | 12/2000 |
| WO | WO-01/47897 A1 | 7/2001 |
| WO | WO-01/60816 A1 | 8/2001 |
| WO | WO-01/64654 A1 | 9/2001 |
| WO | WO-01/64655 A1 | 9/2001 |

(56) References Cited

FOREIGN PATENT DOCUMENTS

| WO | WO-01/85699 A2 | 11/2001 |
|---|---|---|
| WO | WO-02/083653 A1 | 10/2002 |
| WO | WO-03/016306 A1 | 2/2003 |
| WO | WO-03/030909 A1 | 4/2003 |
| WO | WO-03/063794 A2 | 8/2003 |
| WO | WO-03/066601 A1 | 8/2003 |
| WO | WO-2004/014382 A1 | 2/2004 |
| WO | WO-2004/031232 A1 | 4/2004 |
| WO | WO-2004/050068 A1 | 6/2004 |
| WO | WO-2004/056786 A2 | 7/2004 |
| WO | WO-2004/069812 A1 | 8/2004 |
| WO | WO-2004/074244 A2 | 9/2004 |
| WO | WO-2004/080980 A1 | 9/2004 |
| WO | WO-2004/096224 A2 | 11/2004 |
| WO | WO-2005/009443 A1 | 2/2005 |
| WO | WO-2005/013996 A2 | 2/2005 |
| WO | WO-2005/016893 A2 | 2/2005 |
| WO | WO-2005/016894 A1 | 2/2005 |
| WO | WO-2005/026130 A1 | 3/2005 |
| WO | WO-2005/026158 A1 | 3/2005 |
| WO | WO-2005/063722 A1 | 7/2005 |
| WO | WO-2005/070890 A2 | 8/2005 |
| WO | WO-2006/021544 A1 | 3/2006 |
| WO | WO-2006/045066 A2 | 4/2006 |
| WO | WO-2006/053109 A1 | 5/2006 |
| WO | WO-2006/055561 A2 | 5/2006 |
| WO | WO-2006/068770 A1 | 6/2006 |
| WO | WO-2006/074057 A2 | 7/2006 |
| WO | WO-2006/076706 A1 | 7/2006 |
| WO | WO-2006/078846 A1 | 7/2006 |
| WO | WO-2006/101977 A2 | 9/2006 |
| WO | WO-2006/108487 A1 | 10/2006 |
| WO | WO-2006/124874 A2 | 11/2006 |
| WO | WO-2006/128129 A2 | 11/2006 |
| WO | WO-2006/129100 A1 | 12/2006 |
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/120980 A2 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/064274 A1 | 5/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080964 A1 | 7/2008 |
| WO | WO-2008/080965 A2 | 7/2008 |
| WO | WO-2008/088303 A1 | 7/2008 |
| WO | WO-2008/092199 A1 | 8/2008 |
| WO | WO-2008/093687 A1 | 8/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/118823 A2 | 10/2008 |
| WO | WO-2009/012421 A1 | 1/2009 |
| WO | WO-2009/017838 A2 | 2/2009 |
| WO | WO-2009/029682 A1 | 3/2009 |
| WO | WO-2009/032668 A2 | 3/2009 |
| WO | WO-2009/032694 A1 | 3/2009 |
| WO | WO-2009/032703 A1 | 3/2009 |
| WO | WO-2009/080638 A2 | 7/2009 |
| WO | WO-2009/105675 A1 | 8/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/132202 A2 | 10/2009 |
| WO | WO-2009/136995 A2 | 11/2009 |
| WO | WO-2009/143389 A1 | 11/2009 |
| WO | WO-2009/158571 A1 | 12/2009 |
| WO | WO-2010/025833 A1 | 3/2010 |
| WO | WO-2010/081679 A2 | 7/2010 |
| WO | WO-2010/129053 A2 | 11/2010 |
| WO | WO-2011/079231 A1 | 6/2011 |
| WO | WO-2011/090760 A1 | 7/2011 |
| WO | WO-2011/140338 A1 | 11/2011 |
| WO | WO-2011/153514 A2 | 12/2011 |
| WO | WO-2012/021444 A1 | 2/2012 |
| WO | WO-2012/061299 A1 | 5/2012 |
| WO | WO-2012/061303 A1 | 5/2012 |
| WO | WO-2012/061415 A1 | 5/2012 |
| WO | WO-2012/064706 A1 | 5/2012 |
| WO | WO-2012/158843 A2 | 11/2012 |

OTHER PUBLICATIONS

Adeyeye, Moji, ed., Preformulation in Solid Dosage Form Development (Informa Healthcare, 2008) Chapter 2.3, pp. 63-80.*
Gould, International J. of Therapeutics 33, pp. 201-213 & 217 (1986).*
Swarbrick et al., eds. Encyclopedia of Pharmaceutical Technology 13 (Marcel Dekker, NY 1996) pp. 453-499.*
S.L. Morissette et al., Advanced Drug Delivery Reviews, 56,275-300 (2004).*
U.S. Appl. No. 13/518,833, filed Jun. 22, 2012, Gray et al.
U.S. Appl. No. 14/636,905, filed Mar. 3, 2015, Lee et al.
Aliagas-Martin, I. et al., A class of 2,4-bisanilinopyrimidine Aurora A inhibitors with unusually high selectivity against Aurora B, J. Med. Chem. 52:3300-3307 (2009).
Andrulis, I. et al., Neu/ErbB-2 amplification identifies a poor-prognosis group of women with node-negative breast cancer, J Clin Oncol 16:1340-9 (1998).
Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).
Calvo, E. et al., Administration of CI-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).
Carter, T. et al, Inhibition of drug-resistant mutants of ABL, KIT, and EGF receptor kinases, Proc. Natl. Acad. Sci. USA 102(31):11011-11016 (2005).
Cohen, M. et al., Structural bioinformatics-based design of selective, irreversible inhibitors, Science 308:1318-1321 (2005).
Curto, M. et al., Contact-dependent inhibition of EGFR signaling by Nf2/Merlin, J Cell Biol 177:893-903 (2007).
Ding, K. et al., Design, Synthesis and Biological Evaluation of Novel Conformationally Constrained Inhibitors Targeting Epidermal Growth Factor Receptor T790M mutant, J. Med. Chem., Just Accepted Manuscript, 1-36 (2012).
European Search Report for EP10844293.0, 8 pages (Jun. 27, 2013).
European Search Report for EP11816874.9, 5 pages (Dec. 12, 2014).
European Search Report for EP11838624.2, 5 pages (Jun. 6, 2014).
European Search Report for EP11838628.3, 7 pages (Jun. 20, 2014).
European Search Report for EP11839800.7, 8 pages (Jun. 24, 2014).
Fabian, M. et al., A small molecule-kinase interaction map for clinical kinase inhibitors, Nature Biotechnology, 23(3): 329 (2005).
Fallon, K. et al., Constitutive activation of the neuregulin-1/erbB signaling pathway promotes the proliferation of a human peripheral neuroepithelioma cell line, J Neuro Oncol 66:273-84 (2004).
Frank, D., STAT signaling in the pathogenesis and treatment of cancer, Mol. Med. 5 :432-456 (1999).
Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).

(56) References Cited

OTHER PUBLICATIONS

Ghoneim, K., Synthesis and evaluation of some 2-, 4-, di-substituted-6-methylpyrimidine derivatives for antimicrobial activity, J. Indian Chem. Soc. 63(10):914-917 (1986).
Ghosh, D., 2-4-bis (arylamino)-5-methylpyrimidines as antimicrobial agents, J. Med. Chem. 10(5):974 (1967).
Ghosh, D., 2-4-bis (arylamino)-6-methylpyrimidines as antimicrobial agents, J. Indian Chem. Soc. 58(5):512-573 (1981).
Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).
Hur, W. et al., Clinical stage EGFR inhibitors irreversibly alkylate Bmx kinase, Bioorg. Med. Chem. Lett. 18:5916-5919 (2008).
International Search Report for PCT/US09/48784, 8 pages (Nov. 16, 2009).
International Search Report for PCT/US10/31714 dated Aug. 13, 2010.
International Search Report for PCT/US10/62432, 4 pages (May 26, 2011).
International Search Report for PCT/US11/46926, 2 pages (Dec. 22, 2011).
International Search Report for PCT/US11/58610, 4 pages (Mar. 27, 2012).
International Search Report for PCT/US11/58616, 3 pages (Mar. 27, 2012).
International Search Report for PCT/US11/59726, 3 pages (Mar. 20, 2012).
Kirken, R., Targeting Jak3 for immune suppression and allograft acceptance, Transplant. Proc., 33: 3268-3270 (2001).
Kojima, T. et al., Aiming for effective Crystallinity selection in drug development, Journal of Pharmaceutical Science and Technology, Japan, 68(5): 344-349 (2008).
Kumar, A., et al, Structure and Clinical Relevance of the Epidermal Growth Factor Receptor in Human Cancer, Journal of Clinical Oncology 26(10):1742-1751 (2008).
Kwak, E. et al., Irreversible inhibitors of the EGF receptor may circumvent acquired resistance to gefitinib, Proc. Natl. Acad. Sci. USA 102:7665-7670 (2005).
Lajeunesse, D. et al., A systematic screen for dominant second-site modifiers of Merlin/NF2 phenotypes reveals an interaction with blistered/DSRF and scribbler, Genetics 158:667-79 (2001).
Li, D. et al., BIBW2992, an irreversible EGFR/HER2 inhibitor highly effective in preclinical lung cancer models, Oncogene 27:4702-4711 (2008).
Lin, N. and Winer, E., New targets for therapy in breast cancer: Small molecule tyrosine kinase inhibitors, Breast Cancer Res 6:204-210 (2004).
Malaviya, R. et al., Targeting Janus Kinase 3 in Mast Cells Prevents Immediate Hypersensitivity Reactions and Anaphylaxis, J. Biol. Chem. 274 :27028-27038 (1999).
McClatchey, A. and Giovannini, M., Membrane organization and tumorigenesis—the NF2 tumor suppressor, Merlin, Genes Dev 19:2265-77 (2005).
Minkovsky, N. and Berezov, A., BIBW-2992, a dual receptor tyrosine kinase inhibitor for the treatment of solid tumors, Curr Opin Invest Drugs 9:1336-1346 (2008).
Pelton, P. et al., Ruffling membrane, stress fiber, cell spreading and proliferation abnormalities in human Schwann cells, Oncogene 17:2195-2209 (1998).
PubChem CID 44594695. Feb. 1, 2010. [Retrieved from the Internet May 15, 2011: http://pubchem.ncbi.nlm.nih.gov/summary.cgi?cid=44594695&loc=ec_rcs].
Readinger, J. et al., Selective Targeting of ITK Blocks Multiple Steps of HIV Replication, Proc. Natl. Acad. Sci. USA 105: 6684-6689 (2008).
Seidel, H. et al., Pharmaceutical intervention in the JAK/STAT signaling pathway, Oncogene 19: 2645-2656 (2000).
Sequist, L., Second-Generation Epidermal Growth Factor Receptor Tyrosine Kinase Inhibitors in Non-Small Cell Lung Cancer, The Oncologist 12(3):325-330 (2007).
Singh, J. et al, Structure-based design of a potent, selective, and irreversible inhibitor of the catalytic domain of the erbB receptor subfamily of protein tyrosine kinases, J. Med. Chem. 40:1130-1135 (1997).
Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).
Sudbeck, E. et al., Structure-based Design of Specific Inhibitors of Janus Kinase 3 as Apoptosis-inducing Antileukemic Agents, Clin. Cancer Res. 5: 1569-1582 (1999).
Trieu, V. et al., A specific inhibitor of Janus kinase-3 increases survival in a transgenic mouse model of amyotrophic lateral sclerosis, Biochem. Biophys. Res. Commun. 267 :22-25 (2000).
Wong, K. et al, A phase I study with neratinib (HKI-272), an irreversible pan Erb B receptor tyrosine kinase inhibitor, in patients with solid tumors, Clin. Cancer Res. 15(7):2552-2558 (2009).
Written Opinion for PCT/US09/48784, 9 pages (Nov. 16, 2009).
Written Opinion for PCT/US10/31714, 7 pages (Aug. 13, 2010).
Written Opinion for PCT/US10/62432, 6 pages (May 26, 2011).
Written Opinion for PCT/US11/46926, 9 pages (Dec. 22, 2011).
Written Opinion for PCT/US11/58610, 8 pages (Mar. 27, 2012).
Written Opinion for PCT/US11/58616, 9 pages (Mar. 27, 2012).
Written Opinion for PCT/US11/59726, 7 pages (Mar. 20, 2012).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).
Zhou, W. et al. Novel mutant-selective EGFR kinase inhibitors against EGFR T790M, Nature, 462(7276): 1070-1074 (2009).
Elder, D.P. et al., The utility of sulfonate salts in drug development, J Pharm Sci., 99(7): 2948-61 (2010).
U.S. Appl. No. 14/996,874, filed Jan. 15, 2016, Lee et al.
Byrn, S. et al., Pharmaceutical Solids: A strategic Approach to Regulatory Considerations, Pharmaceutical Research, 12(7): 945-954 (1995).
Ludovici, D. W. et al., Evolution of anti-HIV drug candidates. Part 3: Diarylpyrimidine (DAPY) analogues, Bioorganic & Medicinal Chemistry Letters, 11(17): 2235-2239 (2001).
Mordant, C. et al., Synthesis of novel diarylpyrimidine analogues of TMC278 and their antiviral activity against HIV-1 wild-type and mutant strains, Eur. J. Med. Chem., 42(5): 567-579 (2006).
Pearlstein, R. et al., Understanding the structure-activity relationship of the human ether-a-go-go-related gene cardiac K+ channel. A model for bad behavior, Journal of Medicinal Chemistry, 46(11):2017-2022 (2003).
Rebehmed, J. et al., 2D and 3D QSAR studies of diarylpyrimidine HIV-1 reverse transcriptase inhibitors, Journal of Computer-Aided Molecular Design, 22(11): 831-841 (2008).
Sjin, R. et al., In vitro and in vivo characterization of irreversible mutant-selective EGFR inhibitors that are wild-type sparing, Molecular Cancer Therapeutics, 13(6):1468-1479 (2014).
Thakur, A. et al., SAR and QSAR studies: Modelling of new DAPY derivatives, European Journal of Medicinal Chemistry, 43(3): 471-477 (2008).
U.S. Appl. No. 15/080,351, filed Mar. 24, 2016, Singh et al.
U.S. Appl. No. 15/192,491, filed Jun. 24, 2016, Lee et al.
Encyclopedia of Pharmaceutical Technology: Salt Forms Pharmaceutical Aspects, Third Edition, vol. 5, Owen I. Corrigan, Informa Healthcare, 3177-3187 (2007).

* cited by examiner

BESYLATE SALT OF A BTK INHIBITOR

CROSS-REFERENCE TO RELATED APPLICATIONS

The present invention is a continuation application of U.S. application Ser. No. 13/205,062, filed Aug. 8, 2011, now issued as U.S. Pat. No. 8,563,568 on Oct. 22, 2013, which claims priority to US. provisional application Ser. No. 61/372349, filed Aug. 10, 2010, the entirety of each of which is hereby incorporated herein by reference.

FIELD OF THE INVENTION

The present invention provides a salt form, and compositions thereof, useful as inhibitors of protein kinases.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that the novel salt form of the present invention, and compositions thereof, is useful as an inhibitor of one or more protein kinases and exhibits desirable characteristics for the same. In general, this salt form, and pharmaceutically acceptable compositions thereof, is useful for treating or lessening the severity of a variety of diseases or disorders as described in detail herein.

DETAILED DESCRIPTION OF THE INVENTION

Figure 1:
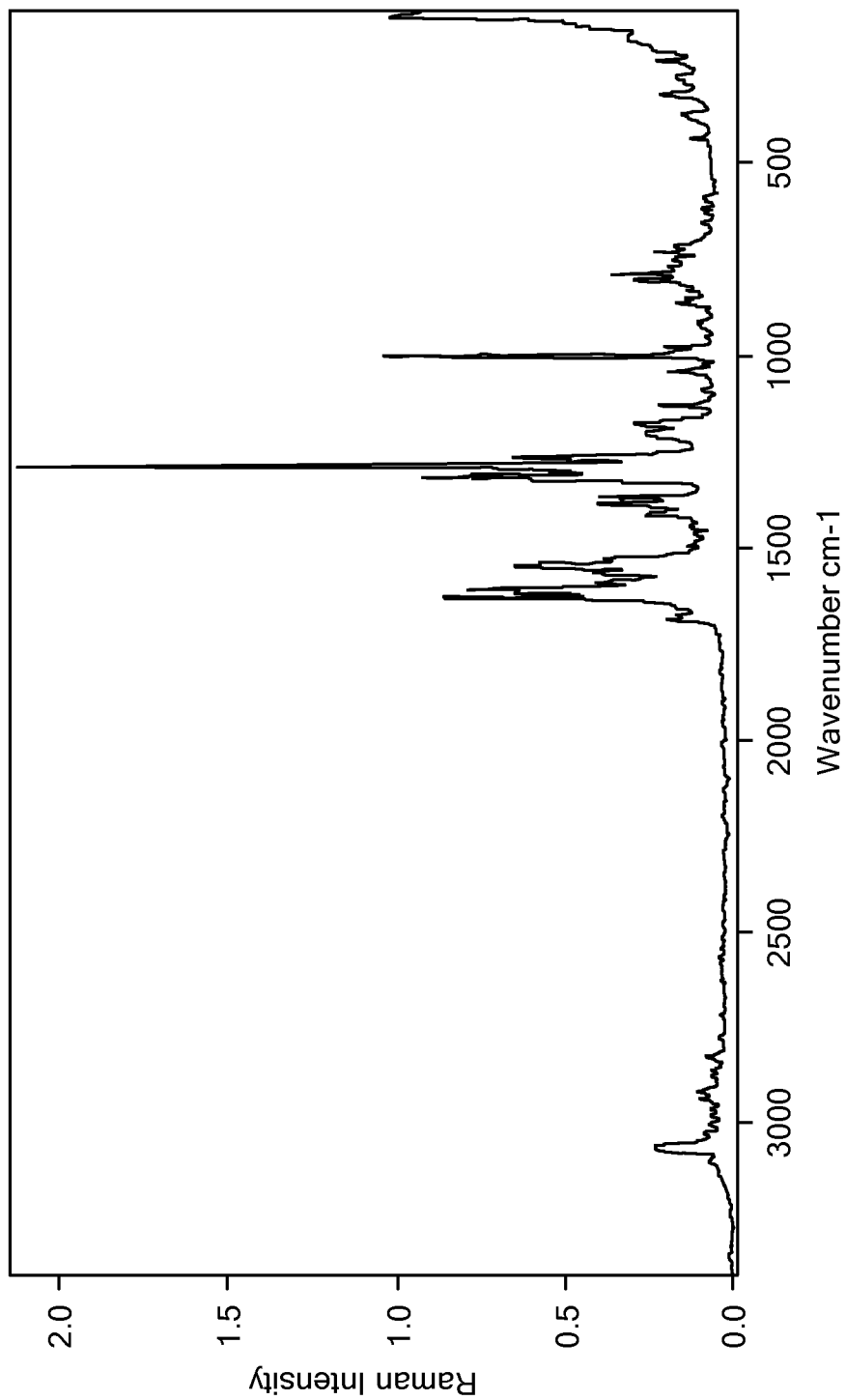
FIG. 1 depicts the FT-Raman spectrum (3400-100 cm$^{-1}$) of Compound 2 Form P1.

General Description of Certain Aspects of the Invention

United States published patent application number US 20100029610, published Feb. 4, 2010 ("the '610 publication," the entirety of which is hereby incorporated herein by reference), describes certain 2,4-disubstituted pyrimidine compounds which covalently and irreversibly inhibit activity of one or more protein kinases, including Bruton's tyrosine kinase ("BTK"), a member of TEC-kinases. Such compounds include compound 1:

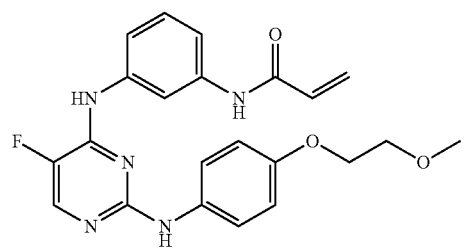

Compound 1 (N-(3-(5-fluoro-2-(4-(2-methoxyethoxy) phenylamino)pyrimidin-4-ylamino)phenyl)acrylamide) is designated as compound number 1-182 and the synthesis of compound 1 is described in detail at Example 20 of the '610 publication.

Compound 1 is active in a variety of assays and therapeutic models demonstrating covalent, irreversible inhibition of BTK (in enzymatic and cellular assays). Notably, compound 1 was found to inhibit B-cell proliferation both in vitro and in vivo. Accordingly, compound 1 is useful for treating one or more disorders associated with activity of BTK.

It would be desirable to provide a salt form of compound 1 that, as compared to compound 1, imparts characteristics such as improved aqueous solubility, stability and ease of formulation. Accordingly, the present invention provides the besylate salt of compound 1.

According to one embodiment, the present invention provides a besylate salt of compound 1, represented by compound 2:

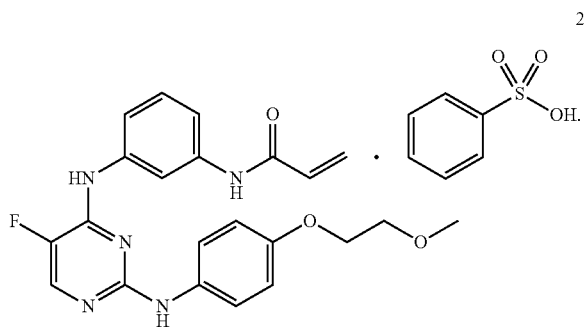

2

It will be appreciated by one of ordinary skill in the art that the benzensulfonic acid and compound 1 are ionically bonded to form compound 2. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary solid forms are described in more detail below.

In other embodiments, the present invention provides compound 2 substantially free of impurities. As used herein, the term "substantially free of impurities" means that the compound contains no significant amount of extraneous matter. Such extraneous matter may include excess benzensulfonic acid, excess compound 1, residual solvents, or any other impurities that may result from the preparation of, and/or isolation of, compound 2. In certain embodiments, at least about 95% by weight of compound 2 is present. In still other embodiments of the invention, at least about 99% by weight of compound 2 is present.

According to one embodiment, compound 2 is present in an amount of at least about 97, 97.5, 98.0, 98.5, 99, 99.5, 99.8 weight percent where the percentages are based on the total weight of the composition. According to another embodiment, compound 2 contains no more than about 3.0 area percent HPLC of total organic impurities and, in certain embodiments, no more than about 1.5 area percent HPLC total organic impurities relative to the total area of the HPLC chromatogram. In other embodiments, compound 2 contains no more than about 1.0% are percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 2 is also meant to include all tautomeric forms of compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

Solid Forms of Compound 2:

It has been found that compound 2 can exist in a variety of solid forms. Such forms include polymorphs, solvates, hydrates, and amorphous. All such forms are contemplated by the present invention. In certain embodiments, the present invention provides compound 2 as a mixture of one or more solid forms selected from polymorphs, solvates, hydrates, and amorphous compound 2.

As used herein, the term "polymorph" refers to the different crystal structures (of unsolvated forms) in which a compound can crystallize. As used herein, the term "solvate" refers to a crystal form with either a stoichiometric or non-stoichiometric amount of solvent is incorporated into the crystal structure. Similarly, the term "hydrate" refers to a crystal form with either a stoichiometric or non-stoichiometric amount of water is incorporated into the crystal structure.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 95% by weight of crystalline compound 2 is present. In still other embodiments of the invention, at least about 99% by weight of crystalline compound 2 is present.

In certain embodiments, compound 2 is a neat crystal form and thus does not have any water or solvent incorporated into the crystal structure. It has been found that compound 2 can exist in at least one distinct neat (i.e., anhydrous) crystal form, or polymorph. In some embodiments, the present invention provides a polymorphic form of Compound 2 referred to herein as Form P1. In certain embodiments, the present invention provides a polymorphic form of Compound 2 referred to herein as Form P22.

In certain embodiments, the present invention provides Form P1 of Compound 2. According to one aspect, Form P1 of Compound 2 has a powder X-ray diffraction pattern substantially similar to that depicted in FIG. 2. According to another embodiment, Form P1 of compound 2 is characterized in that it has one or more peaks in its powder X-ray diffraction pattern selected from those at about 6.21, about 9.48, and about 13.29 degrees 2-theta. In some embodiments, Form P1 of compound 2 is characterized in that it has two or more peaks in its powder X-ray diffraction pattern selected from those at about 6.21, about 9.48, and about 13.29 degrees 2-theta. Form P1 of compound 2 is characterized in that it has all three peaks in its powder X-ray diffraction pattern selected from those at about 6.21, about 9.48, and about 13.29 degrees 2-theta.

As used herein, the term "about", when used in reference to a degree 2-theta value refers to the stated value ±0.1 degree 2-theta. Methods for preparing Form P1 of compound 2 are described infra.

In certain embodiments, the present invention provides Form P22 of Compound 2. According to one aspect, Form P22 of Compound 2 has a powder X-ray diffraction pattern substantially similar to that depicted in FIG. 6. According to another embodiment, Form P22 of compound 2 is characterized in that it has one or more peaks in its powder X-ray diffraction pattern selected from those at about 7.29, about 8.38, and about 11.12 degrees 2-theta. In some embodiments, Form P22 of compound 2 is characterized in that it has two or more peaks in its powder X-ray diffraction pattern selected from those at about 7.29, about 8.38, and about 11.12 degrees 2-theta. Form P22 of compound 2 is characterized in that it has all three peaks in its powder X-ray diffraction pattern selected from those at about 7.29, about 8.38, and about 11.12 degrees 2-theta.

In some embodiments, Form P22 is characterized in a melting point of 194° C. Methods for preparing Form P22 of compound 2 are described infra.

According to another embodiment, the present invention provides compound 2 as an amorphous solid. Amorphous solids are well known to one of ordinary skill in the art and are typically prepared by such methods as lyophilization, melting, and precipitation from supercritical fluid, among others.

General Methods of Providing Compound 2:

Compound 1 is prepared according to the methods described in detail in the '610 publication, the entirety of which is hereby incorporated herein by reference. Compound 2 is prepared from Compound 1, according to the Scheme below.

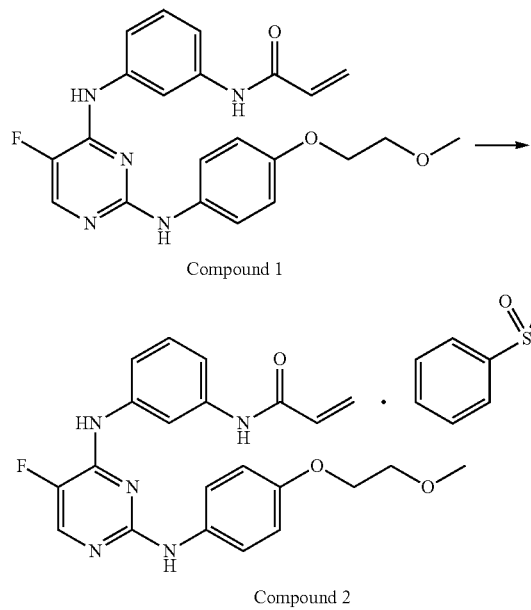

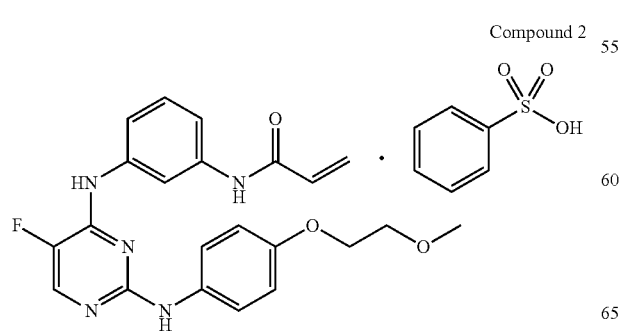

Compound 2

As depicted in the general Scheme above, Compound 2 is prepared from Compound 1 by combining Compound 1 with benzenesulfonic acid to form the besylate salt thereof. Thus, another aspect of the present invention provides a method for preparing Compound 2:

comprising the steps of:
providing Compound 1:

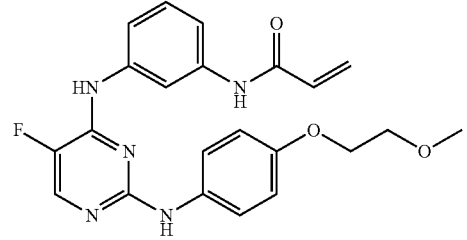

Compound 1 combining Compound 1 with benzenesulfonic acid in a suitable solvent; and
optionally isolating Compound 2.

A suitable solvent may solubilize one or more of the reaction components, or, alternatively, the suitable solvent may facilitate the agitation of a suspension of one or more of the reaction components. Examples of suitable solvents useful in the present invention are a protic solvent, a polar aprotic solvent, or mixtures thereof. In certain embodiments, suitable solvents include an ether, an ester, an alcohol, a ketone, or a mixture thereof. In certain embodiments, the suitable solvent is methanol, ethanol, isopropanol, or acetone wherein said solvent is anhydrous or in combination with water or heptane. In other embodiments, suitable solvents include tetrahydrofuran, dimethylformamide, dimethylsulfoxide, glyme, diglyme, methyl t-butyl ether, t-butanol, n-butanol, and acetonitrile. In another embodiment, the suitable solvent is anhydrous ethanol. In some embodiments, the suitable solvent is MTBE.

According to another embodiment, the present invention provides a method for preparing Compound 2:

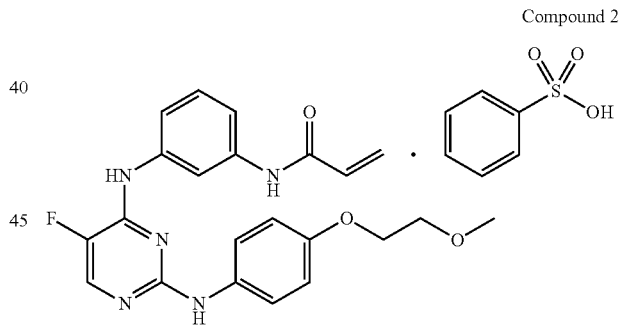

Compound 2 comprising the steps of:
combining Compound 1:

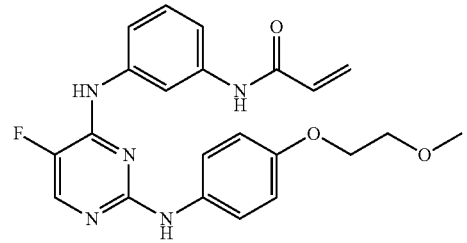

Compound 1 with a suitable solvent and optionally heating to form a solution thereof;

adding benzenesulfonic acid to said solution; and
optionally isolating Compound 2.

As described generally above, Compound 1 is dissolved in a suitable solvent, optionally with heating. In certain embodiments Compound 1 is dissolved at about 50 to about 60° C. In other embodiments, Compound 1 is dissolved at about 50 to about 55° C. In still other embodiments, compound 1 is dissolved at the boiling temperature of the solvent. In other embodiments, compound 1 is dissolved without heating.

In certain embodiments, about 1 equivalent of benzenesulfonic acid is added to Compound 1 to afford Compound 2. In other embodiments, less than 1 equivalent of benzenesulfonic acid is added to compound 1 to afford Compound 2. In yet other embodiments, greater than 1 equivalent of benzenesulfonic acid is added to Compound 1 to afford Compound 2. In still other embodiments, about 0.9 to about 1.1 equivalents of benzenesulfonic acid is added to Compound 1 to afford Compound 2. In another embodiment, about 0.99 to about 1.01 equivalents of benzenesulfonic acid is added to Compound 1 to afford Compound 2.

It will be appreciated that the benzenesulfonic acid may be added to the mixture of Compound 1 and a suitable solvent in any suitable form. For example, the benzenesulfonic acid may be added in solid form or as a solution or a suspension in a suitable solvent. The suitable solvent may be the same suitable solvent as that which is combined with Compound 1 or may be a different solvent. According to one embodiment, the benzenesulfonic acid is added in solid form. In certain embodiments, the benzenesulfonic acid combined with a suitable solvent prior to adding to Compound 1. According to another embodiment, the benzenesulfonic acid is added as a solution in a suitable solvent. In other embodiments, the suitable solvent in which benzenesulfonic acid is dissolved is a polar protic or polar aprotic solvent. Such solvents include water, alcohols, ethers, and ketones. Examples of such solvents include water, methanol, ethanol, isopropanol, acetone, tetrahydrofuran, dimethylformamide, dimethylsulfoxide, glyme, diglyme, methyl t-butyl ether, t-butanol, n-butanol, and acetonitrile. In certain embodiments the suitable solvent is selected from those above and is anhydrous. According to one embodiment, the benzenesulfonic acid is dissolved in MTBE.

In certain embodiments, the resulting mixture containing Compound 2 is cooled. In other embodiments, the mixture containing Compound 2 is cooled below 20° C.

In certain embodiments, Compound 2 precipitates from the mixture. In another embodiment, Compound 2 crystallizes from the mixture. In other embodiments, Compound 2 crystallizes from solution following seeding of the solution (i.e., adding crystals of Compound 2 to the solution).

Crystalline Compound 2 can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, Compound 2 is optionally isolated. It will be appreciated that Compound 2 may be isolated by any suitable physical means known to one of ordinary skill in the art. In certain embodiments, precipitated solid compound 2 is separated from the supernatant by filtration. In other embodiments, precipitated solid Compound 2 is separated from the supernatant by decanting the supernatant.

In certain embodiments, precipitated solid Compound 2 is separated from the supernatant by filtration.

In certain embodiments, isolated Compound 2 is dried in air. In other embodiments isolated Compound 2 is dried under reduced pressure, optionally at elevated temperature.

Uses, Formulation and Administration
Pharmaceutically Acceptable Compositions

According to another embodiment, the invention provides a composition comprising Compound 2 and a pharmaceutically acceptable carrier, adjuvant, or vehicle. The amount of Compound 2 in compositions of this invention is such that is effective to measurably inhibit a protein kinase, particularly at least one of a TEC-kinase, or a mutant thereof, in a biological sample or in a patient. In certain embodiments, the amount of Compound 2 in compositions of this invention is such that is effective to measurably inhibit at least one of TEC-kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

The amount of compounds of the present invention that may be combined with the carrier materials to produce a composition in a single dosage form will vary depending upon the host treated, the particular mode of administration. In certain embodiments, provided compositions are formulated so that a dosage of between 0.01-100 mg/kg body weight/day of Compound 2 can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of Compound 2 in the composition will also depend upon the particular compound in the composition.

Uses of Compounds and Pharmaceutically Acceptable Compositions

Compound 2 and compositions described herein are generally useful for the inhibition of protein kinase activity of one or more enzymes. Examples of kinases that are inhibited by Compound 2 and compositions described herein and against which the methods described herein are useful include BTK and other TEC-kinases, including ITK, TEC, BMX and RLK, or a mutant thereof.

Bruton's tyrosine kinase ("BTK"), a member of TEC-kinases, is a key signaling enzyme expressed in all hematopoietic cell types except T lymphocytes and natural killer cells. BTK plays an essential role in the B-cell signaling pathway linking cell surface B-cell receptor (BCR) stimulation to downstream intracellular responses.

BTK is a key regulator of B-cell development, activation, signaling, and survival (Kurosaki, Curr Op Imm, 2000, 276-281; Schaeffer and Schwartzberg, Curr Op Imm 2000, 282-288). In addition, BTK plays a role in a number of other hematopoietic cell signaling pathways, e.g., Toll like receptor (TLR) and cytokine receptor-mediated TNF-a production in macrophages, IgE receptor (Fc_epsilon_RI) signaling in mast cells, inhibition of Fas/APO-1 apoptotic signaling in B-lineage lymphoid cells, and collagen-stimulated platelet aggregation. See, e.g., C. A. Jeffries, et al., (2003), Journal of Biological Chemistry 278:26258-26264; N. J. Horwood, et al., (2003), The Journal of Experimental Medicine 197: 1603-1611; Iwaki et al. (2005), Journal of Biological Chemistry 280(48):40261-40270; Vassilev et al. (1999), Journal of Biological Chemistry 274(3): 1646-1656, and Quek et al. (1998), Current Biology 8(20): 1137-1140.

Patients with mutations in BTK have a profound block in B cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased serum levels of IgM and IgG3. BTK deletion in mice has a profound effect on B cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc_epsilon_RI). BTK deficient murine mast cells have reduced degranulation and decreased production of proinflammatory cytokines following Fc_epsilon_RI cross-linking (Kawakami et al. Journal of Leukocyte Biology 65: 286-290).

Compound 2 is an inhibitor of BTK and therefore useful for treating one or more disorders associated with activity of BTK. Thus, in some embodiments, the present invention provides a method for treating a BTK-mediated disorder comprising the step of administering to a patient in need thereof. Compound 2, or pharmaceutically acceptable composition thereof.

As used herein, the term "BTK-mediated" disorders or conditions as used herein means any disease or other deleterious condition in which BTK, or a mutant thereof, is known to play a role. Accordingly, another embodiment of the present invention relates to treating or lessening the severity of one or more diseases in which BTK, or a mutant thereof, is known to play a role. Specifically, the present invention relates to a method of treating or lessening the severity of a disease or condition selected from a proliferative disorder or an autoimmune disorder, wherein said method comprises administering to a patient in need thereof. Compound 2 or a composition according to the present invention.

In some embodiments, the present invention provides a method for treating or lessening the severity of one or more diseases and conditions associated with BTK. In some embodiments, the disease or condition is an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia. In some embodiments, the disease or condition is a hyperproliferative disease or immunologically-mediated diseases including rejection of transplanted organs or tissues and Acquired Immunodeficiency Syndrome (AIDS, also known as HIV).

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In some embodiments, the present invention provides a method for treating or lessening the severity of one or more diseases and conditions associated with BTK, wherein the disease or condition is selected from a cancer. In one embodiment, the cancer is a B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis. In some embodiments, the cancer is breast cancer, prostate cancer, or cancer of the mast cells (e.g., mastocytoma, mast cell leukemia, mast cell sarcoma, systemic mastocytosis). In one embodiment, the cancer is bone cancer. In another embodiment, the cancer is of other primary origin and metastasizes to the bone.

In some embodiments, the present invention provides a method for treating or lessening the severity of one or more diseases or conditions associated with BTK including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with BTK, wherein the disease or condition is selected from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In some embodiments, the present invention provides a method for treating or lessening the severity of one or more diseases and conditions associated with BTK, including infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In some embodiments, the present invention provides a method for treating or lessening the severity of one or more diseases and conditions associated with BTK, selected from rheumatoid arthritis, multiple sclerosis, diabetes, B-cell chronic lymphocytic leukemia, acute lymphocytic leukemia, hairy cell leukemia, non-Hodgkin's lymphoma, Hodgkin's lymphoma, multiple myeloma, bone cancer, colorectal cancer, pancreatic cancer, bone metastasis, osteoporosis, irritable bowel syndrome, Crohn's disease, lupus and renal transplant.

BTK is a member of the TEC-kinases, which members share a common cysteine at the equivalent position of Cys481 of Btk also capable of irreversible inhibition as described in the '610 publication. Accordingly, examples of kinases that are inhibited by Compound 2 and compositions described herein and against which the methods described herein are useful include additional TEC-kinases beyond BTK, including ITK, TEC, BMX and RLK, or a mutant thereof.

The activity of Compound 2 as an inhibitor of a TEC-kinase, or a mutant thereof, may be assayed in vitro, in vivo or in a cell line. In vitro assays include assays that determine inhibition of either the phosphorylation activity and/or the subsequent functional consequences, or ATPase activity of activated a TEC-kinase, or a mutant thereof. Alternate in vitro assays quantitate the ability of Compound 2 to bind to a TEC-kinase Inhibitor binding may be measured by radiolabeling the inhibitor prior to binding, isolating the inhibitor/TEC-kinase (i.e., TEC, BTK, ITK, RLK and BMX complex and determining the amount of radiolabel bound. Detailed conditions for assaying Compound 2 as an inhibitor of a TEC-kinase, or a mutant thereof, are set forth in detail in the '610 publication.

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The TEC family of non-receptor tyrosine kinases, referred to herein as "TEC-kinases," plays a central role in signaling through antigen-receptors such as the TCR, BCR and Fc receptors (reviewed in Miller A, et al. Current Opinion in Immunology 14; 331-340 (2002). TEC-kinases are essential for T cell activation. Three members of the family, Itk, Rlk and, are activated downstream of antigen receptor engagement in T cells and transmit signals to downstream effectors, including PLC-γ. Combined deletion of Itk and Rlk in mice leads to a profound inhibition of TCR responses including proliferation, cytokine production and immune responses to an intracellular parasite (*Toxoplasma gondii*) (Schaeffer et al., Science 284; 638-641 (1999)). Intracellular signalling following TCR engagement is effected in ITK/RLK deficient T cells; inositol triphosphate production, calcium mobilization and MAP kinase activation are all reduced. Tec-kinases are also essential for B cell development and activation.

TEC-kinases include five family members, which are expressed primarily in hematopoietic cells: TEC, BTK, ITK (also known as TSK and EMT), RLK (also known as TXK), and BMX (also known as ETK). Additional related TEC-kinases have been found in *Drosophila melanogaster*, zebrafish (*Danio rerió*), skate (*Raja eglanteria*), and sea urchin (*Anthocidaris crassispina*).

Compound 2 is an inhibitor of one of more TEC-kinases and is therefore useful for treating one or more disorders associated with activity of one or more TEC-kinases. Thus, in certain embodiments, the present invention provides a method for treating a TEC-mediated disorder comprising the step of administering to a patient in need thereof. Compound 2, or pharmaceutically acceptable composition thereof.

The term "TEC-mediated condition", as used herein means any disease or other deleterious condition in which TEC-kinases are known to play a role. Such conditions include those described herein and in Melcher, M et al., "The Role of TEC Family Kinases in Inflammatory Processes", *Anti-Inflammatory & Anti-Allergy Agents in Medicinal Chemistry*, Vol. 6, No. 1, pp. 61-69 (February 2007). Accordingly, another embodiment of the present invention relates to treating or lessening the severity of one or more diseases in which TEC-kinases are known to play a role. Specifically, the present invention relates to a method of treating or lessening the severity of a disease or condition selected from autoimmune, inflammatory, proliferative, and hyperproliferative diseases and immunologically-mediated diseases including rejection of transplanted organs or tissues and Acquired Immunodeficiency Syndrome (AIDS) (also known as HIV), wherein said method comprises administering to a patient in need thereof. Compound 2 or a composition thereof.

In some embodiments, the present invention provides a method for treating or lessening the severity of one or more diseases and conditions associated with TEC-kinases including diseases of the respiratory tract including, without limitation, reversible obstructive airways diseases including asthma, such as bronchial, allergic, intrinsic, extrinsic and dust asthma, particularly chronic or inveterate asthma (e.g., late asthma airways hyper-responsiveness) and bronchitis.

In some embodiments, the present invention provides a method for treating or lessening the severity of one or more diseases and conditions associated with TEC-kinases including those conditions characterized by inflammation of the nasal mucus membrane, including acute rhinitis, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung, and idiopathic interstitial pneumonia.

In some embodiments, the present invention provides a method for treating or lessening the severity of one or more diseases and conditions associated with TEC-kinases including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with TEC-kinases including diseases and disorders of the skin, including, without limitation, psoriasis, systemic sclerosis, atopical dermatitis, contact dermatitis and other eczematous dermatitis, seborrhoetic dermatitis, Lichen planus, pemphigus, bullous pemphigus, epidermolysis bullosa, urticaria, angiodermas, vasculitides, erythemas, cutaneous eosinophilias, uveitis, alopecia, greata and vernal conjunctivitis.

In some embodiments, the present invention provides a method for treating or lessening the severity of one or more diseases and conditions associated with TEC-kinases including diseases and disorders of the gastrointestinal tract, including, without limitation, celiac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

In some embodiments, the present invention provides a method for treating or lessening the severity of one or more diseases and conditions associated with TEC-kinases including those diseases and disorders of other tissues and systemic disease, including, without limitation, multiple sclerosis, artherosclerosis, lupus erythematosus, systemic lupus erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas, and prostate cancers), and artherosclerosis.

In some embodiments, the present invention provides a method for treating or lessening the severity of one or more diseases and conditions associated with TEC-kinases including allograft rejection including, without limitation, acute and chronic allograft rejection following for example transplantation of kidney, heart, liver, lung, bone marrow, skin and cornea; and chronic graft versus host disease.

In some embodiments, the present invention relates to a method of treating or lessening the severity of one or more of the diseases or conditions associated with TEC-kinases, as recited above, wherein said method comprises administering to a patient in need thereof. Compound 2 or a composition according to the present invention.

Compound 2 and compositions thereof, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compound 2 and compositions of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to Compound 2, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of Compound 2 of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing Compound 2 of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, Compound 2 is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Compound 2 can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting a TEC-kinase, or a mutant thereof, activity in a biological sample comprising the step of contacting said biological sample with Compound 2, or a composition comprising said compound. In certain embodiments, the invention relates to a method of irreversibly inhibiting a TEC-kinase, or a mutant thereof, activity in a biological sample comprising the step of contacting said biological sample with Compound 2, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from a TEC-kinase, or a mutant thereof, activity in a biological sample is useful for a variety of purposes that are known to one of skill in the art. Examples of such purposes include, but are not limited to, blood transfusion, organ transplantation, biological specimen storage, and biological assays.

Another embodiment of the present invention relates to a method of inhibiting protein kinase activity in a patient comprising the step of administering to said patient Compound 2, or a composition comprising said compound.

According to another embodiment, the invention relates to a method of inhibiting one or more of a TEC-kinase, or a mutant thereof, activity in a patient comprising the step of administering to said patient Compound 2, or a composition comprising said compound. According to certain embodiments, the invention relates to a method of irreversibly inhibiting one or more of a TEC-kinase, or a mutant thereof, activity in a patient comprising the step of administering to said patient Compound 2, or a composition comprising said compound. In other embodiments, the present invention provides a method for treating a disorder mediated by one or more of a TEC-kinase, or a mutant thereof, in a patient in need thereof, comprising the step of administering to said patient Compound 2 or pharmaceutically acceptable composition thereof. Such disorders are described in detail herein.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures

Powder X-ray diffraction patterns were obtained on a Bruker D8 Advance with Cu—Kα radiation and LynxEye detector. The powder samples were deposited on a zero-background polished silicon sample holder and was rotated during measurement. Measurements performed as follows: 40 kV/40 mA tube power, 0.02° 2-theta step size, 37 second step time, and 2.5-50° 2-theta scanning range.

Proton Nuclear Magnetic Resonance ($^1$H NMR) spectra were obtained on a Bruker model DPX-300 MHz NMR spectrometer. $^1$H NMR spectra were recorded at 300.13 MHz, using a 30 degree excitation pulse, with a pulse delay of 1 second, 16 scans. Deuterated DMSO was used as solvent.

DSC data were obtained on a Perkin Elmer DSC 7 using closed gold crucibles. The sample was filled and dried under nitrogen. The instrument heated the sample at −50° C. to 250° C. at 10K/min.

TG-FTIR data were obtained using a Netzsch Thermo-Microbalance TG 209 with a Bruker FT-IR Spectrometer Vector 22. Samples were measured on an aluminum crucible (with microhole) under nitrogen atmosphere and heated from 25-250° C. at 10K/min Example 1

Preparation of Compound 2 (Form P1)

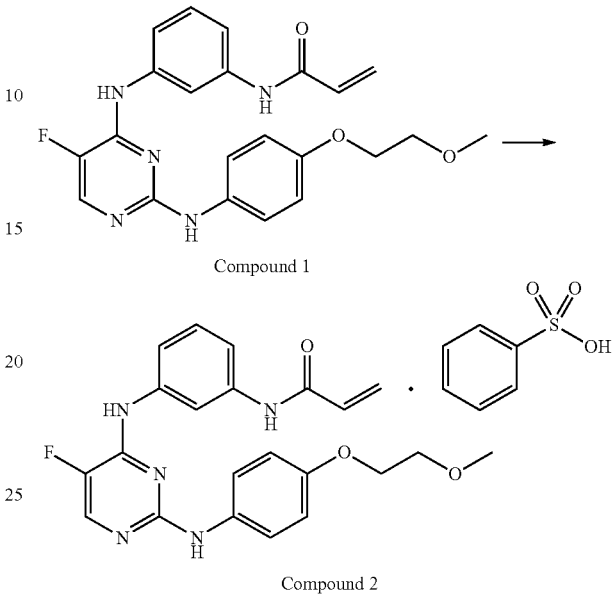

Compound 1 is prepared according to the method described in detail in at Example 20 of the '610 publication., the entirety of which is hereby incorporated herein by reference.

The besylate salt of Compound 1, i.e., Compound 2, was prepared as follows. Compound 1 was added to MTBE under nitrogen to form a slurry and the mixture heated to 50-55° C. Benzenesulfonic acid, in MTBE, was added and the resulting mixture stirred for one hour. The mixture was cooled to 0-5° C. and allowed to stir for an hour. The resulting solids were collected by filtration and then dried at 65-70° C. under vacuum to afford Compound 2. Characterization of the resulting material demonstrated that the Compound 2 was crystalline and this crystalline form referred to as Form P1.

FT-Raman spectrum for Compound 2, Form P1 is depicted in FIG. 1.

Figure 2:
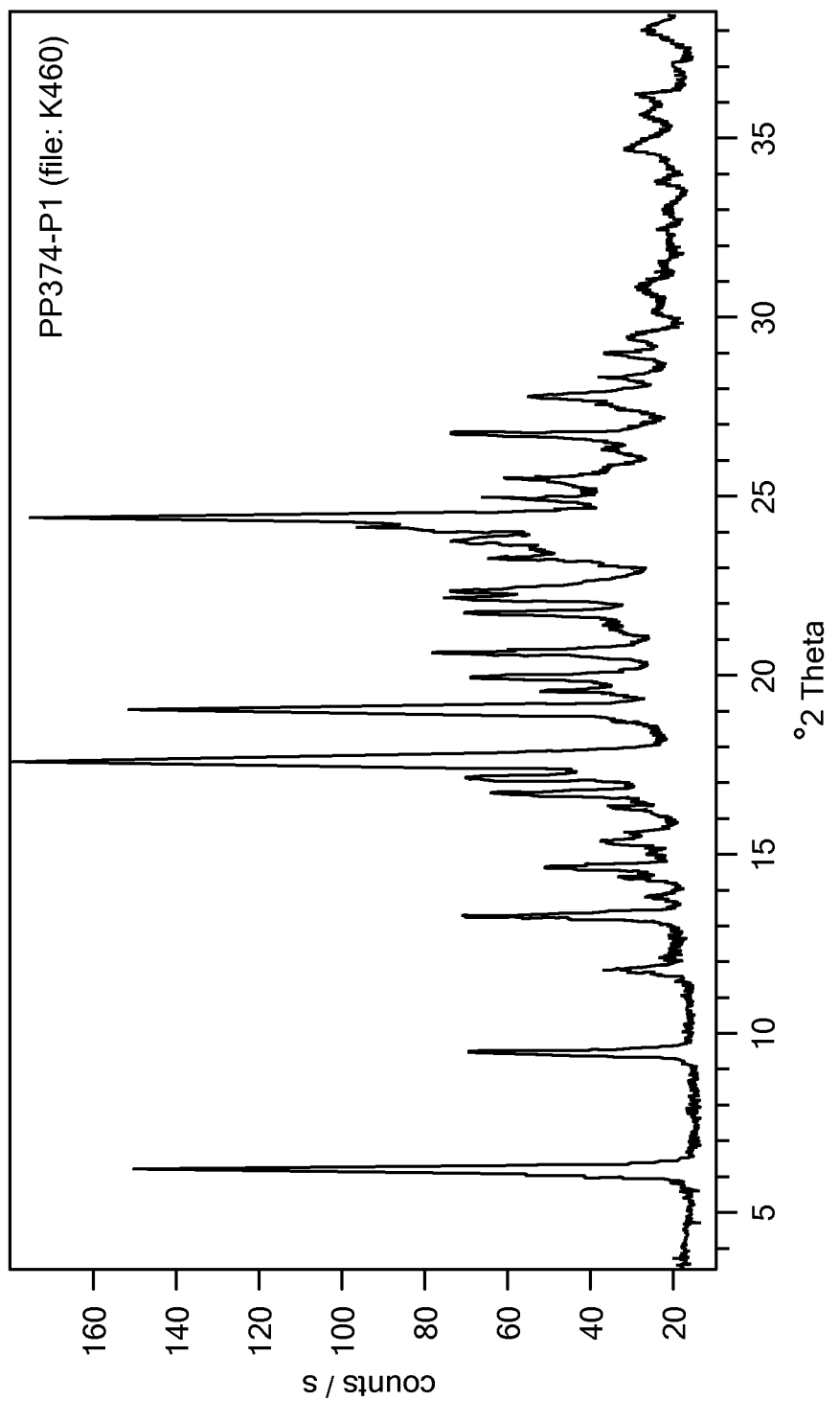
FIG. 2 depicts the PXRD pattern of Compound 2 Form P1.

PXRD for Compound 2, Form P1 is depicted in FIG. 2. Table 1 below sets out the X-ray diffraction peaks observed for Form P22 of compound 2 wherein each value is in degrees 2-theta.

TABLE 1

| Observed X-ray diffraction peaks for Compound 2 (Form P1) 2-Theta |
|---|
| 6.21 |
| 9.48 |
| 11.79 |
| 13.29 |
| 14.67 |
| 16.71 |
| 17.18 |
| 17.59 |
| 19.07 |
| 19.60 |
| 19.96 |
| 20.70 |

TABLE 1-continued

Observed X-ray diffraction peaks for Compound 2 (Form P1)
2-Theta 21.78
22.21
23.33
23.82
24.19
24.44
24.99
25.47
26.78
27.89

Figure 3:
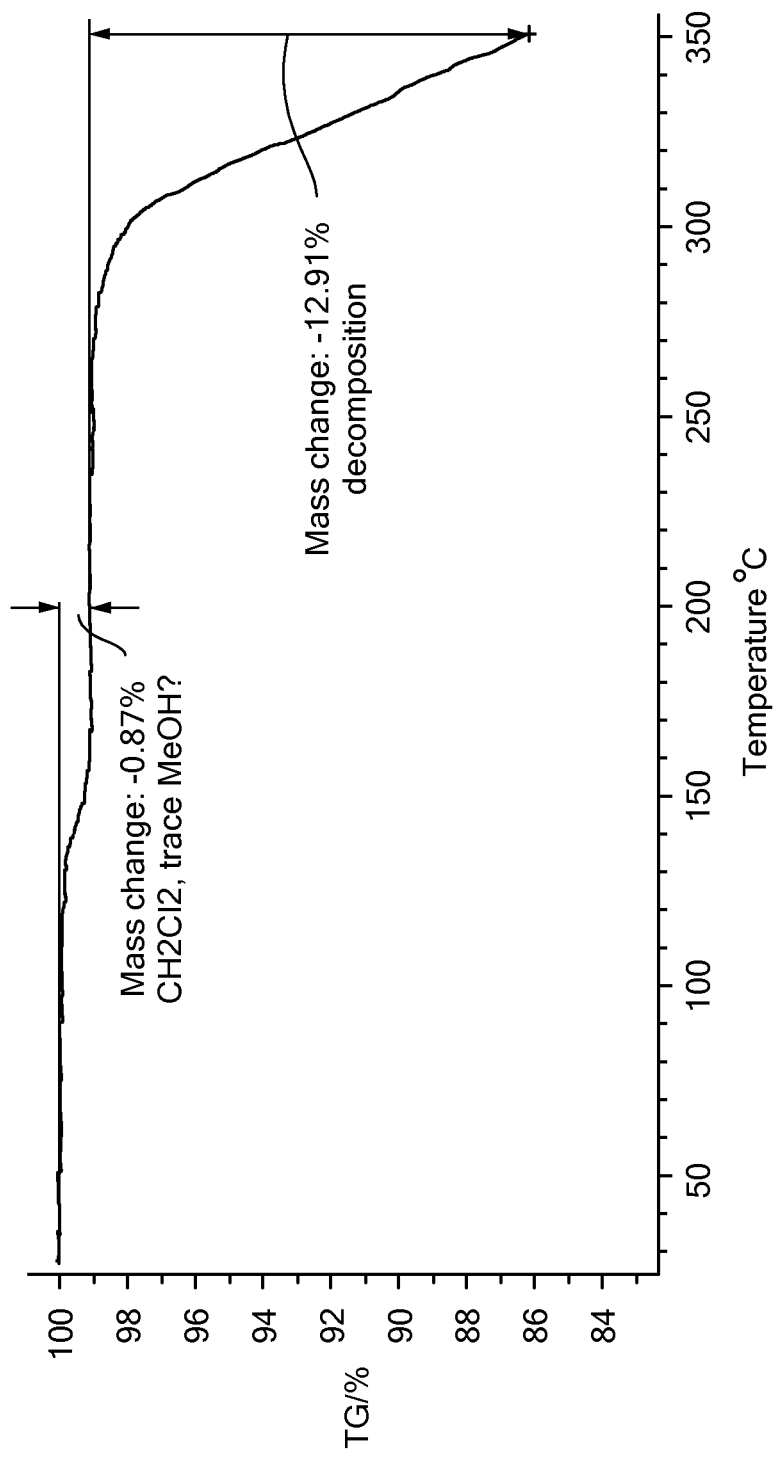
FIG. 3 depicts the TG-FTIR of Compound 2 Form P1.

TG-FTIR for Compound 2, Form P1 is depicted in FIG. 3. The resulting thermogram shows the loss of about 0.9 weight % dichloromethane (residual solvent) in a step from 130-160° C.

Figure 4:
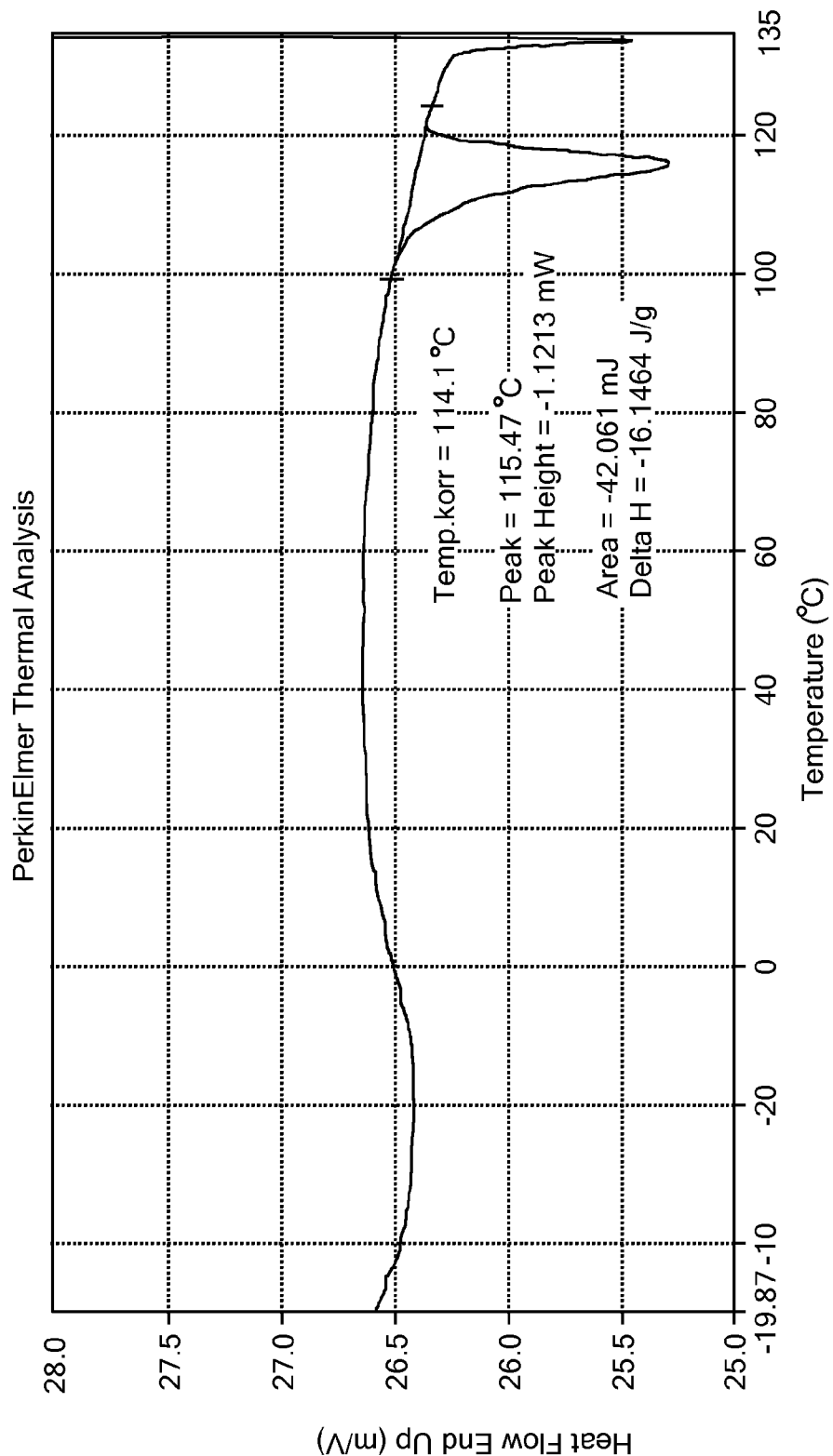
FIG. 4 depicts the DSC thermogram of Compound 2 Form P1 showing cooling step.
Figure 5:
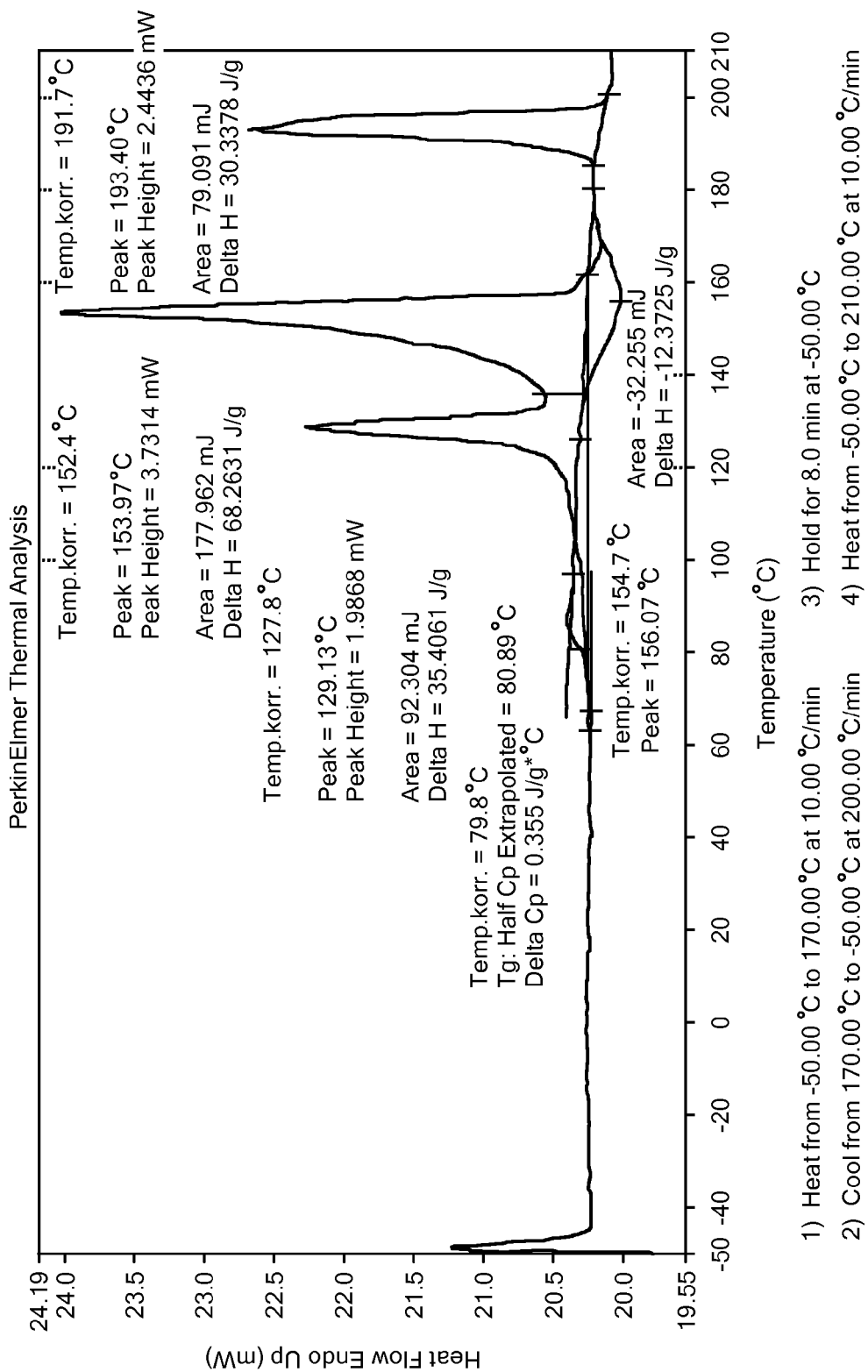
FIG. 5 depicts the DSC thermogram of Compound 2 Form P1 showing the four-step heating and cooling process.

DSC for Compound 2, Form P1 is depicted in FIG. 4 and FIG. 5.

Example 2

Solubility of Compound 2

Solubility of Compound 2, at room temperature, was measured in seventeen solvents and two solvent mixtures by manual dilution combined with visual observation. The results are summarized in Table 2, below.

TABLE 2

Solubilities of Compound 2

| Solvent | Solubility mg/mL |
| --- | --- |
| Water | <1 |
| Toluene | <1 |
| TBME | <1 |
| 1,4-dioxane | <1 |
| Ethyl Acetate | <1 |
| $CH_2Cl_2$ | <1 |
| Isopropanol | <1 |
| Anisole | <1 |
| $CH_3CN$ | ~2 |
| Ethanol | ~2 |
| THF | ~2 |
| Acetone | ~2.5 |
| Ethylene Glycol | 22 < S < 17 |
| Methanol | 26 < S < 29 |
| Benzyl alcohol | 97 < S < 194 |
| DMF | >184 |
| Pyridine | >234 |
| 1:1 DMF:$H_2O$ | 71 < S < 106 |
| 3:7 DMF:$H_2O$ | 16 < S < 18 |

Example 3

Preparation of Compound 2 (Form P22)

Figure 6:
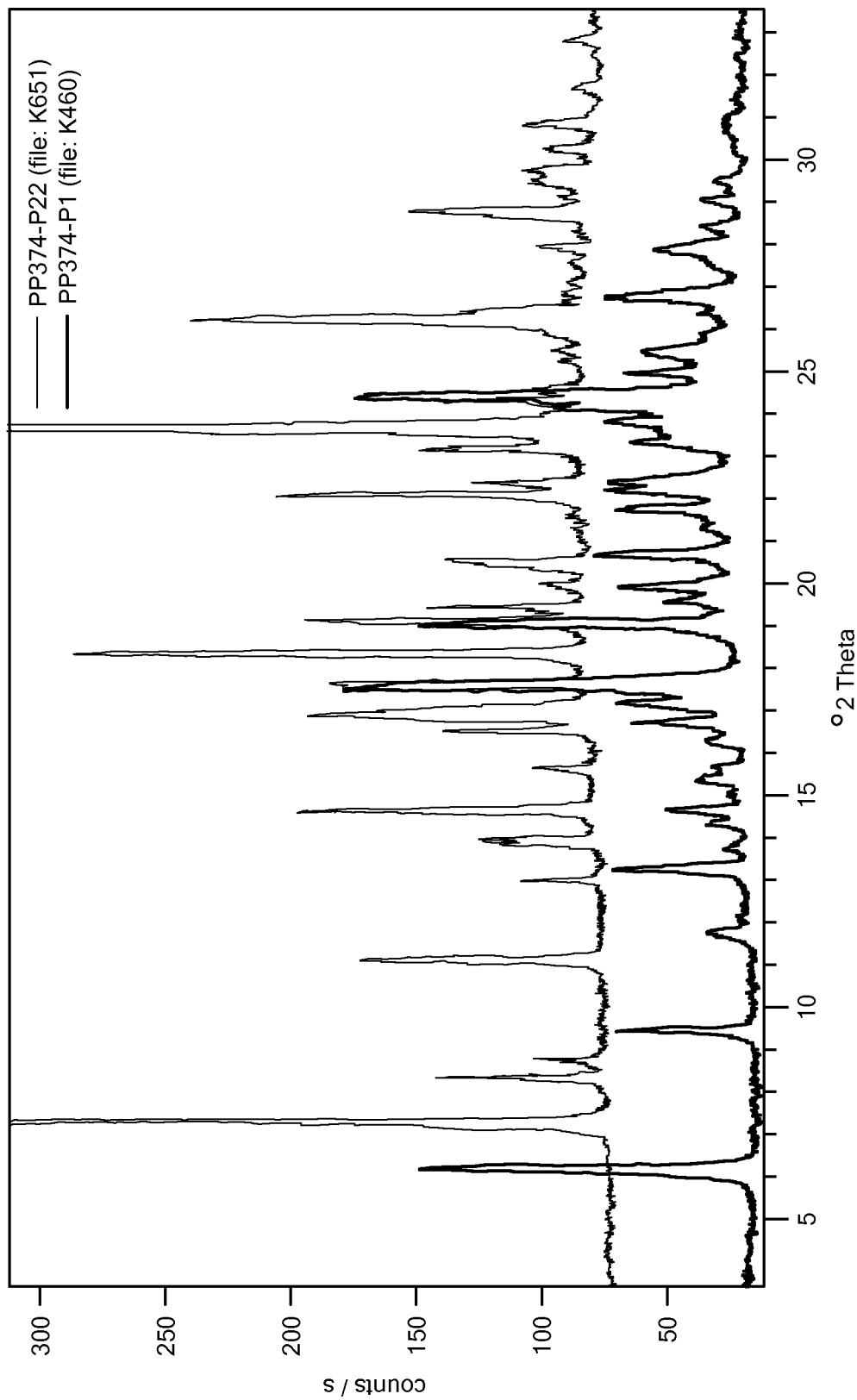
FIG. 6 depicts the PXRD pattern of Compound 2 Form P22 compared to the PXRD pattern of Compound 2 Form P1.
Figure 7:
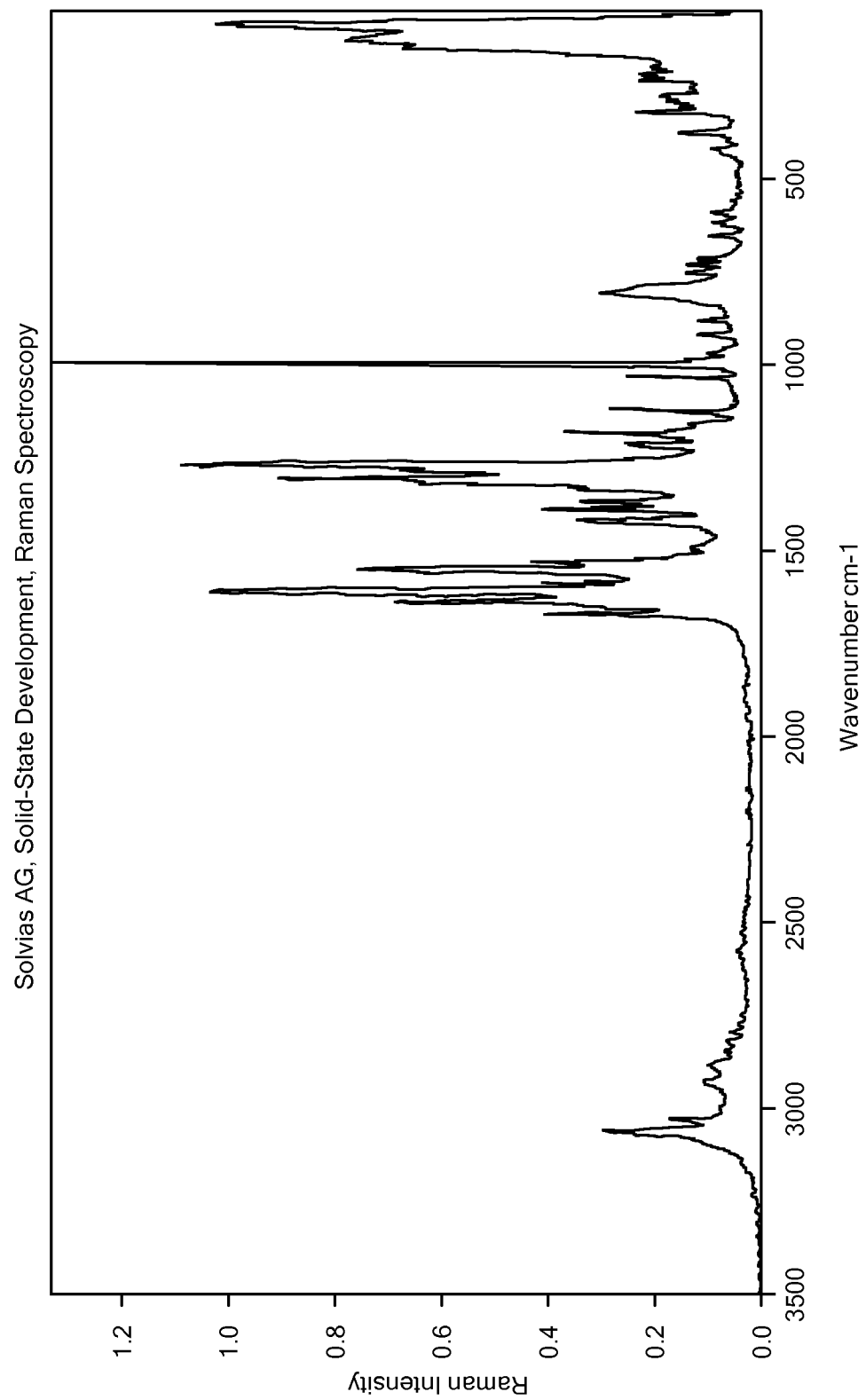
FIG. 7 depicts the FT-Raman spectrum (3400-100 cm$^{-1}$) of Compound 2 Form P22.
Figure 8:
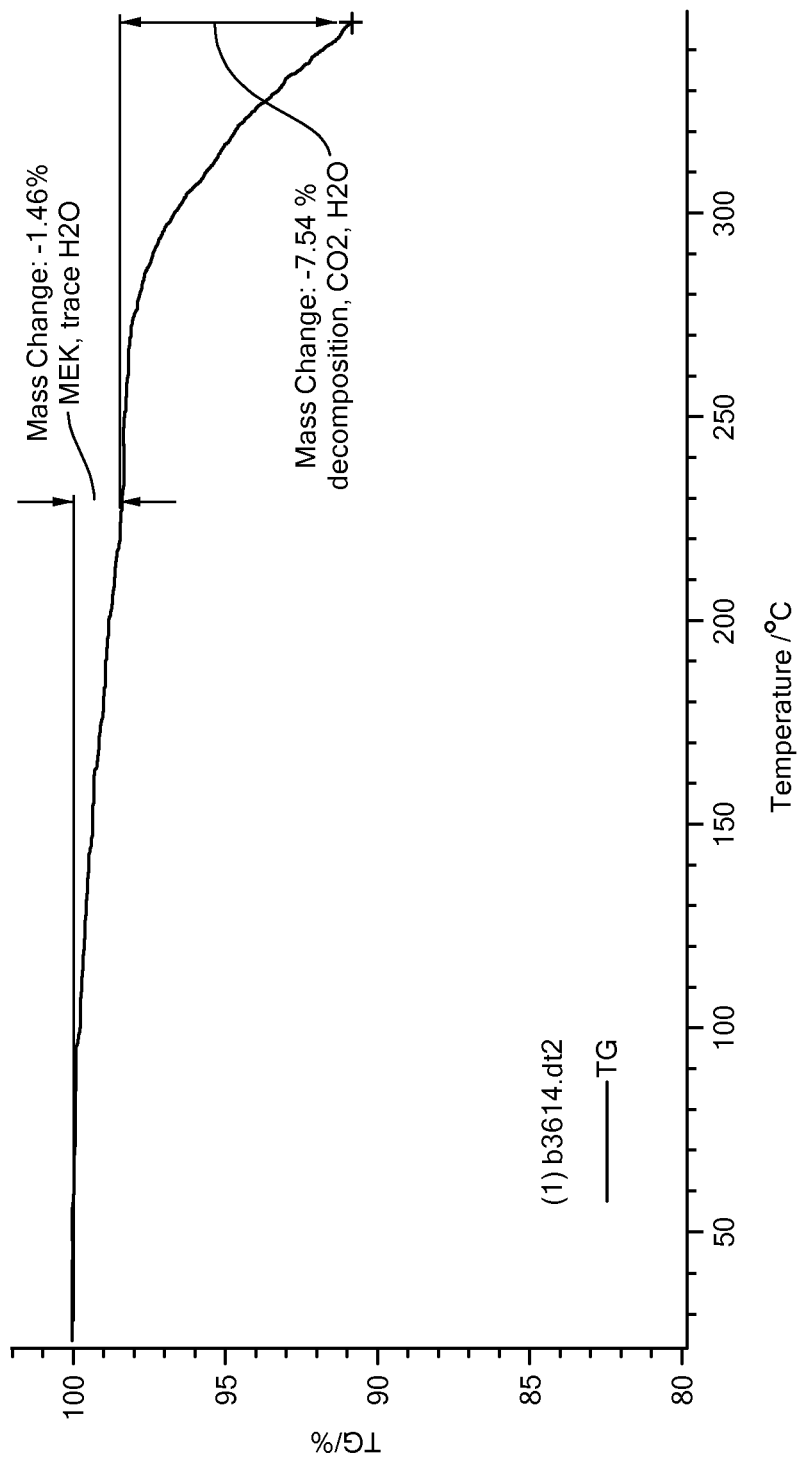
FIG. 8 depicts the TG-FTIR of Compound 2 Form P22.
Figure 9:
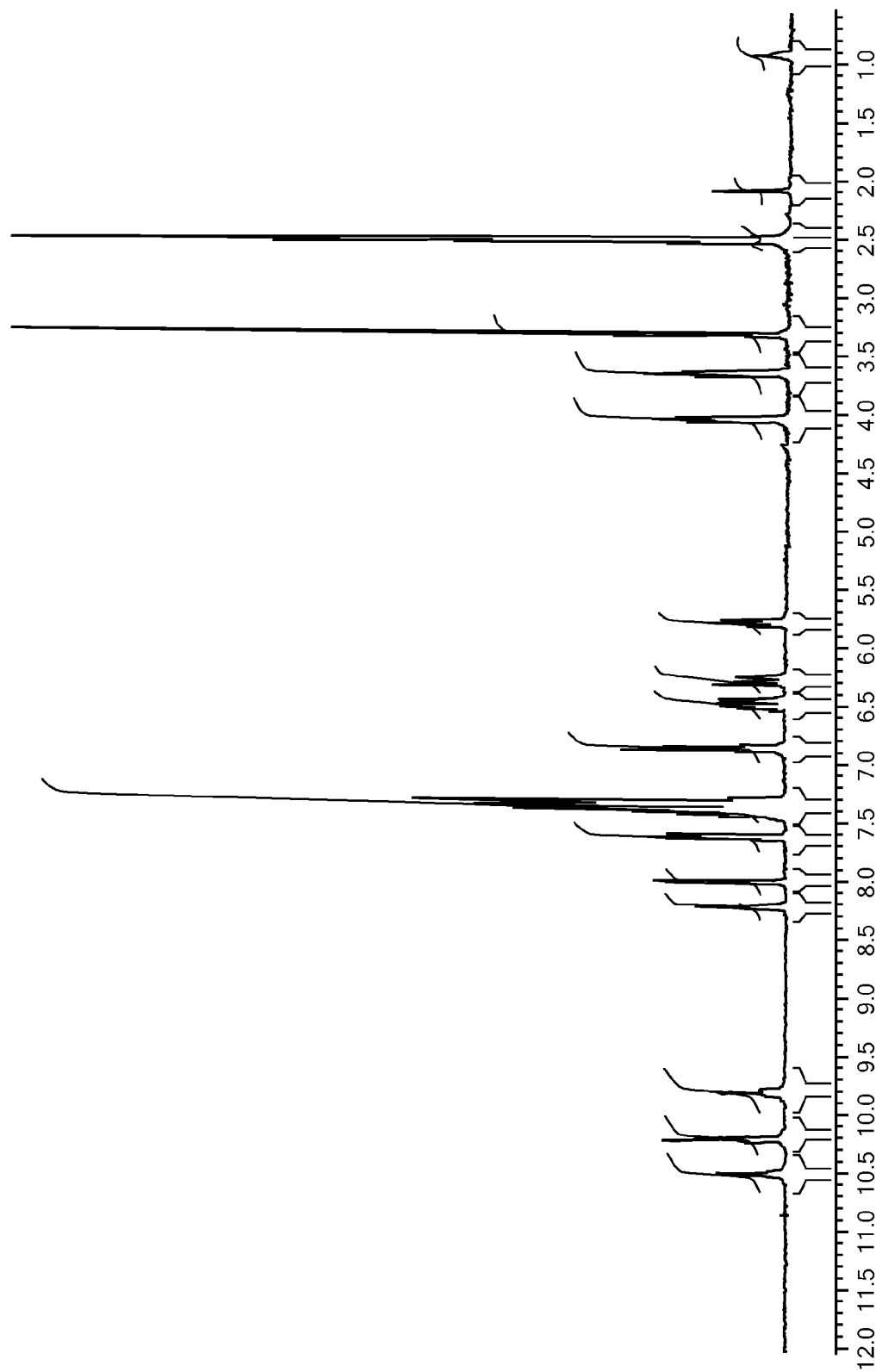
FIG. 9 depicts the $^1$H NMR of Compound 2 Form P22 prepared according to Example 3, infra.
Figure 10:
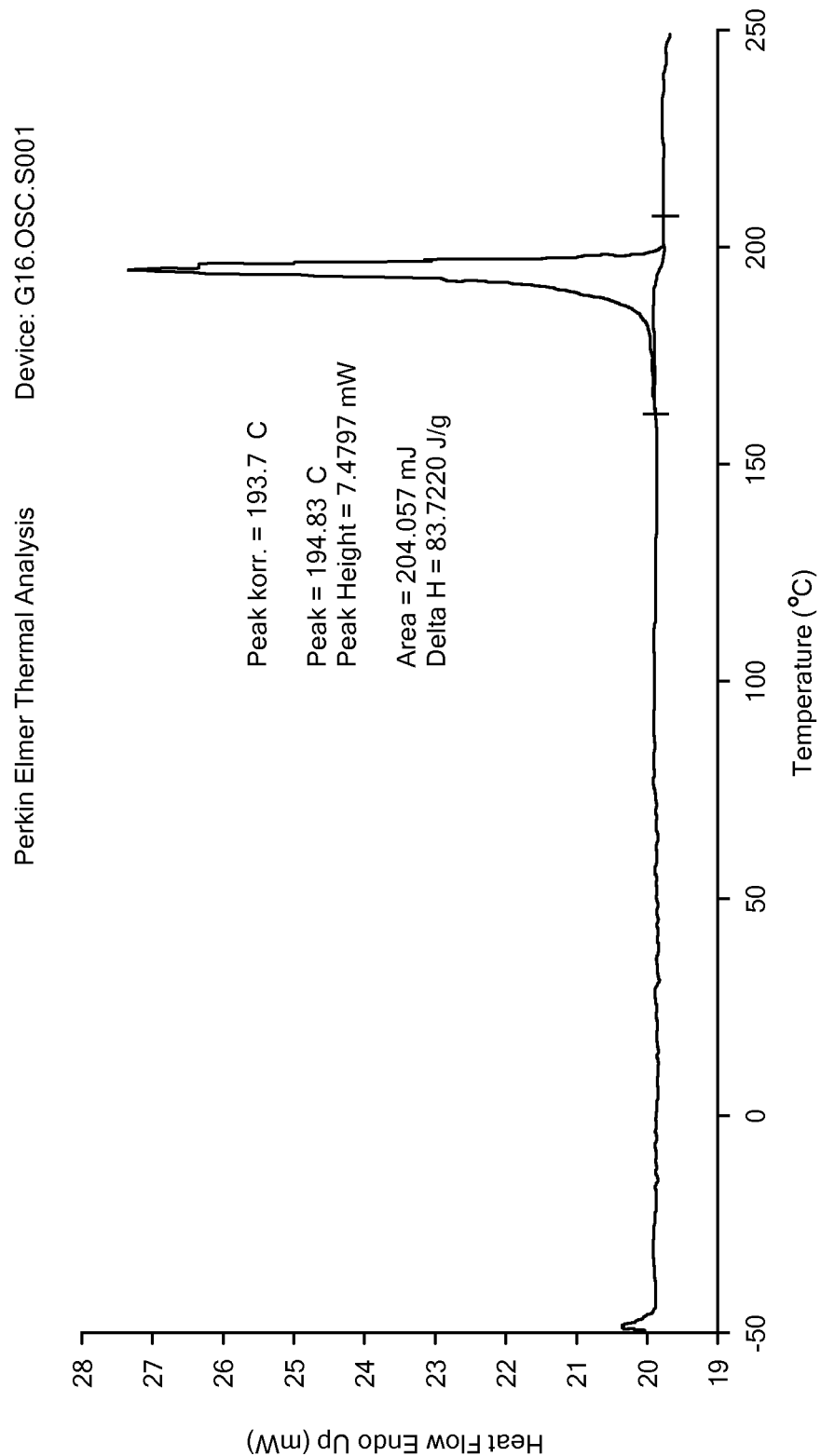
FIG. 10 depicts the DSC thermogram of Compound 2 Form P22

Compound 2 (82.2 mg) was suspended in methyl ethyl ketone (6 mL) and the suspension heated to 68° C. while adding 8 mL methyl ethyl ketone. A clear solution was obtained and heated to 75° C. The solution was cooled to 5° C. and solvent partially evaporated to obtain a white precipitate. The resulting solid was recovered by filter centrifugation to afford form P22. The material was characterized and the results as follows:

The PXRD pattern of Compound 2 Form P22, as compared to Form P1, is depicted in FIG. 6. The FT-Raman spectrum of Form P22 is depicted in FIG. 7. The TG-FTIR spectrum of Form P22 is depicted in FIG. 8. The $^1$H NMR of Form P22 is depicted in FIG. 9 and is consistent with the structure of Compound 2 having 1:1 ratio with its besylate salt. The DSC thermogram is depicted in FIG. 10 and shows a single endothermic event at 193.7° C.

Table 3 below sets out the X-ray diffraction peaks observed for Form P22 of Compound 2 wherein each value is in degrees 2-theta.

TABLE 3

Observed X-ray diffraction peaks for Compound 2 (Form P22)
2-Theta 7.29
8.38
8.79
11.12
12.99
13.88
14.65
15.57
16.56
16.89
17.04
17.69
18.35
19.10
19.43
20.00
20.53
22.08
22.38
23.21
23.66
24.34
24.60
26.22
27.93
28.78
29.76

We claim:
1. Compound 2:

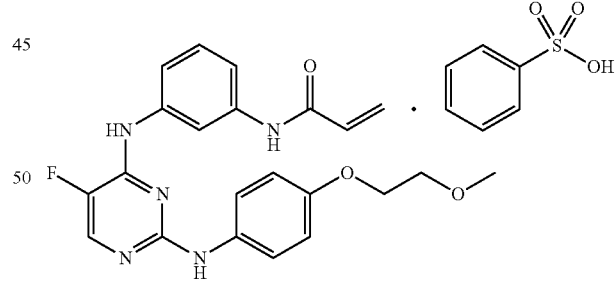

2. The compound according to claim 1, wherein said compound is in solid form.
3. The compound according to claim 2, wherein said compound is crystalline.
4. The compound according to claim 3, wherein said compound is a crystalline solid substantially free of amorphous Compound 2.
5. The compound according to claim 1, wherein said compound is substantially free of impurities.
6. A composition comprising the compound according to claim 1 and a pharmaceutically acceptable carrier or excipient.

7. The compound according to claim 2, wherein the solid form of the compound is characterized by at least one peak selected from the Form P1PXRD spectra depicted in FIG. 2.

8. The compound according to claim 7, wherein the solid form of the compound is characterized by at least two peaks selected from the Form P1PXRD spectra depicted in FIG. 2.

9. The compound according to claim 8, wherein the solid form of the compound is characterized by at least three peaks selected from the Form P1PXRD spectra depicted in FIG. 2.

10. The compound according to claim 9, wherein the solid form of the compound is characterized by at least four peaks selected from the Form P1PXRD spectra depicted in FIG. 2.

11. The compound according to claim 2, wherein the solid form of the compound is characterized by at least one peak selected from the Form P22PXRD spectra depicted in FIG. 6.

12. The compound according to claim 11, wherein the solid form of the compound is characterized by at least two peaks selected from the Form P22PXRD spectra depicted in FIG. 6.

13. The compound according to claim 12, wherein the solid form of the compound is characterized by at least three peaks selected from the Form P22PXRD spectra depicted in FIG. 6.

14. The compound according to claim 13, wherein the solid form of the compound is characterized by at least four peaks selected from the Form P22PXRD spectra depicted in FIG. 6.

* * * * *

UNITED STATES PATENT AND TRADEMARK OFFICE
CERTIFICATE OF CORRECTION

PATENT NO. : 9,604,936 B2
APPLICATION NO. : 14/058847
DATED : March 28, 2017
INVENTOR(S) : Witowski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 78 days.

Signed and Sealed this
Twenty-fifth Day of September, 2018

Andrei Iancu
*Director of the United States Patent and Trademark Office*